(12) United States Patent
Heflich (10) Patent No.: US 10,842,742 B1
(45) Date of Patent: Nov. 24, 2020

(54) DISSOLVED C60 AND METHOD OF PRODUCING DISSOLVED C60

(71) Applicant: Innovation for Success, LLC, Doylestown, PA (US)

(72) Inventor: Leonard W. Heflich, Doylestown, PA (US)

(73) Assignee: Innovation for Success, LLC, Doylestown, PA (US)

( * ) Notice: Subject to any disclaimer, the term of this patent is extended or adjusted under 35 U.S.C. 154(b) by 0 days.

(21) Appl. No.: 16/819,552

(22) Filed: Mar. 16, 2020

Related U.S. Application Data (60) Provisional application No. 62/884,198, filed on Aug. 8, 2019.

(51) Int. Cl.
| | |
|---|---|
| *A61K 9/00* | (2006.01) |
| *A61K 47/02* | (2006.01) |
| *A61K 47/06* | (2006.01) |
| *C01B 32/156* | (2017.01) |
| *B82Y 30/00* | (2011.01) |
| *B82Y 40/00* | (2011.01) |

(52) U.S. Cl.
CPC .............. *A61K 9/006* (2013.01); *A61K 47/02* (2013.01); *A61K 47/06* (2013.01); *B82Y 30/00* (2013.01); *B82Y 40/00* (2013.01); *C01B 32/156* (2017.08)

(58) Field of Classification Search
None
See application file for complete search history.

(56) References Cited

U.S. PATENT DOCUMENTS

| | | | |
|---|---|---|---|
| 9,663,734 B2 * | 5/2017 | Rostro | ............... C09K 5/00 |
| 2003/0162837 A1 | 8/2003 | Dugan et al. | |
| 2019/0083622 A1 | 3/2019 | Raderman et al. | |
| 2019/0133994 A1 | 5/2019 | Smith et al. | |

OTHER PUBLICATIONS

Konopelko et al., Russian Journal of General Chemistry (2014), 84(2), pp. 205-208.*
Bakry, Rania et al., Medicinal applications of fullerenes, Institute of Analytical Chemistry and Radiochemistry, Leopold-Franzens University, Innsbruck, Austria, 12 pages, 2007.
Chistyakov et al., Possible Mechanism of Fullerene C60 Antioxidant Action, Hindawi Publishing Corporation, BioMed Research International, 5 pages, vol. 2013.
Liu et al, The applications of buckminsterfullerence C60 and derivatives in orthopaedic research, Connect Tissue Res., 20 pages, Apr. 2014.
Markovic et al., Biomedical potential of the reactive oxygen species generation and quenching by fullerenes (C60), Vinca Institute of Nuclear Sciences, Laboratory for Atomic Physics, 13 pages, 2008.

* cited by examiner

*Primary Examiner* — Brian J Davis
(74) *Attorney, Agent, or Firm* — Maginot, Moore & Beck LLP (57) ABSTRACT

A method of dissolving C60 molecules including combining C60 molecules with a limonene composition to form a C60 mixture, and heating the C60 mixture to a predetermined temperature for a predetermined time period to dissolve the C60 molecules into the limonene composition to form a dissolved C60 mixture. The dissolved C60 mixture is homogenous and includes at least 16.67 mg of the dissolved C60 molecules per milliliter of the limonene composition.

7 Claims, 9 Drawing Sheets

DISSOLVED C60 AND METHOD OF PRODUCING DISSOLVED C60

This application claims the benefit of priority of U.S. provisional application Ser. No. 62/884,198, filed on Aug. 8, 2019 the disclosure of which is herein incorporated by reference in its entirety.

FIELD

This disclosure relates to the field of nanomaterials and, in particular, to dissolving nanomaterials in a liquid medium suitable for therapeutic, nutritional, and medicinal applications.

BACKGROUND

Nanomaterials are materials of which a single unit is sized, in at least one dimension, from approximately one nanometer (1 nm) to approximately one thousand nanometers (1,000 nm) and often from approximately one nanometer (1 nm) to approximately one hundred nanometers (100 nm). One type of nanomaterial or sub-nanomaterial is the C60 molecule, which is also referred to as C.60, C-60, $C_{60}$, Buckminsterfullerene, fullerene, and buckyballs. The C60 molecule is an allotrope of carbon and consists of carbon atoms connected by single and double bonds so as to form a closed mesh. Each C60 molecule includes sixty atoms of carbon arranged in a soccer ball-like shape that includes twenty hexagons and twelve pentagons with a carbon atom at each vertex of each hexagon and pentagon. The C60 molecules have a diameter of approximately 0.72 nm; thus, C60 is typically referred to as either a nanomaterial or a sub-nanomaterial.

C60 is typically formed through a combustion process that isolates C60 molecules from soot. To prepare C60 for therapeutic or nutritional usage, the C60 is mixed with an edible oil, such as olive oil, for example. Known processes for mixing C60 in olive oil are extremely time consuming and expensive because C60 dissolves only to a trivial extent in olive oil. Specifically, the solubility of C60 in olive oil is no more than approximately 0.9 mg/ml. Moreover, when C60 is mixed with olive oil, the C60 tends to agglomerate and to resist dissolution. To overcome this issue, researchers sonicate and stir the C60 and olive oil mixture for five to ten days to attempt to break up clumps of the C60. Even after this extremely lengthy process, however, only a trivial amount of the C60 becomes dissolved in the olive oil with the remainder of the C60 molecules packed together in microscopic clumps. As such, only a trivial amount of the C60 in the olive oil mixture is bioactive and most of the C60 is unavailable for therapeutic, nutritional, and medicinal benefits. Moreover, the mixture of olive oil and C60 is subject to settling and reagglomeration (i.e. the olive oil and C60 mixture is unstable), thereby further reducing therapeutic and nutritional benefits of the C60.

Based on the above, further developments in the area of preparing C60 for therapeutic, nutritional, and medical applications are desired.

SUMMARY

According to an exemplary embodiment of the disclosure a method of dissolving C60 molecules includes combining C60 molecules with a limonene composition to form a C60 mixture, and heating the C60 mixture to a predetermined temperature for a predetermined time period to dissolve the C60 molecules into the limonene composition to form a dissolved C60 mixture. The dissolved C60 mixture is homogenous and includes at least 16.67 mg of the dissolved C60 molecules per milliliter of the limonene composition.

According to another exemplary embodiment of the disclosure, a method of preparing an orally dissolving thin film including dissolved C60 molecules includes combining C60 molecules with a limonene composition to form a C60 mixture, heating the C60 mixture to a predetermined temperature for a predetermined time period to dissolve the C60 molecules into the limonene composition to form a dissolved C60 mixture, and combining the dissolved C60 mixture with a thin film liquid to form a thin film mixture. The method further includes forming an orally dissolvable thin film from the thin film mixture. The dissolved C60 mixture is homogenous and includes at least 16.67 mg of the dissolved C60 molecules per milliliter of the limonene composition.

According to a further exemplary embodiment of the disclosure, a dissolved C60 mixture includes a plurality of C60 molecules dissolved in a limonene composition. The dissolved C60 mixture is stable, such that no settling or precipitating of the dissolved C60 molecules occurs in the limonene composition.

In the dissolved state, C60 molecules have many potential therapeutic, nutritional, and medicinal applications. Progress in applying C60 molecules, however, has thus far been hampered by the fact that C60 molecules are insoluble in aqueous media. To date, only inedible and toxic solvents have shown any significant ability to solubilize and/or dissolve C60 molecules without chemical modification or derivatization, which changes the nature and action of the C60 molecule.

The disclosure describes a breakthrough in preparing solubilized C60 for therapeutic, nutritional, and medicinal applications. Specifically, it was discovered that C60 is highly soluble/dissolvable in limonene and d-limonene, which are referred to herein as a limonene composition. The limonene composition is an edible and non-toxic liquid in which C60 molecules readily dissolve when the mixture is heated. The resultant dissolved C60 mixture is produced in a matter of minutes (about thirty minutes, in one embodiment) and, therefore, is many times faster and easier to produce than the mixture of C60 and olive oil. Additionally, the dissolved C60 mixture disclosed herein is stable and includes C60 molecules homogeneously dispersed throughout the mixture. Thus, the dissolved C60 mixture is a huge advancement over the C60 and olive oil mixture, which is unstable (i.e. subject to settling and reagglomeration) and includes C60 molecules in a clumped, non-uniform, and nonhomogeneous mixture. The dissolved C60 mixture disclosed herein is particularly useful in applications in which a specific quantity of C60 molecules are dosed, such as for therapeutic, nutritional, and medical applications.

The dissolved C60 mixture is a safe and edible mixture including C60 molecules at a sufficient concentration and stability to be practical in preparing test applications. The method disclosed herein does not change the nature, action, and structure of the C60 molecule. Additionally, using the dissolved C60 mixture to prepare a liposomal dispersion creates a convenient, stable, and safe aqueous solution of C60 molecules. The method disclosed herein produces a water soluble C60 mixture in a convenient, safe, stable, and inexpensive way. The method is a dramatic improvement over previous attempts to improve the solubility of C60, such as by derivatizing C60 with hydroxyl groups to create a Fullerol.

DETAILED DESCRIPTION

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Aspects of the disclosure are disclosed in the accompanying description. Alternate embodiments of the disclosure and their equivalents may be devised without parting from the spirit or scope of the disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

As used herein, the term "approximately" means within plus or minus 5% of the stated value.

Figure 1:
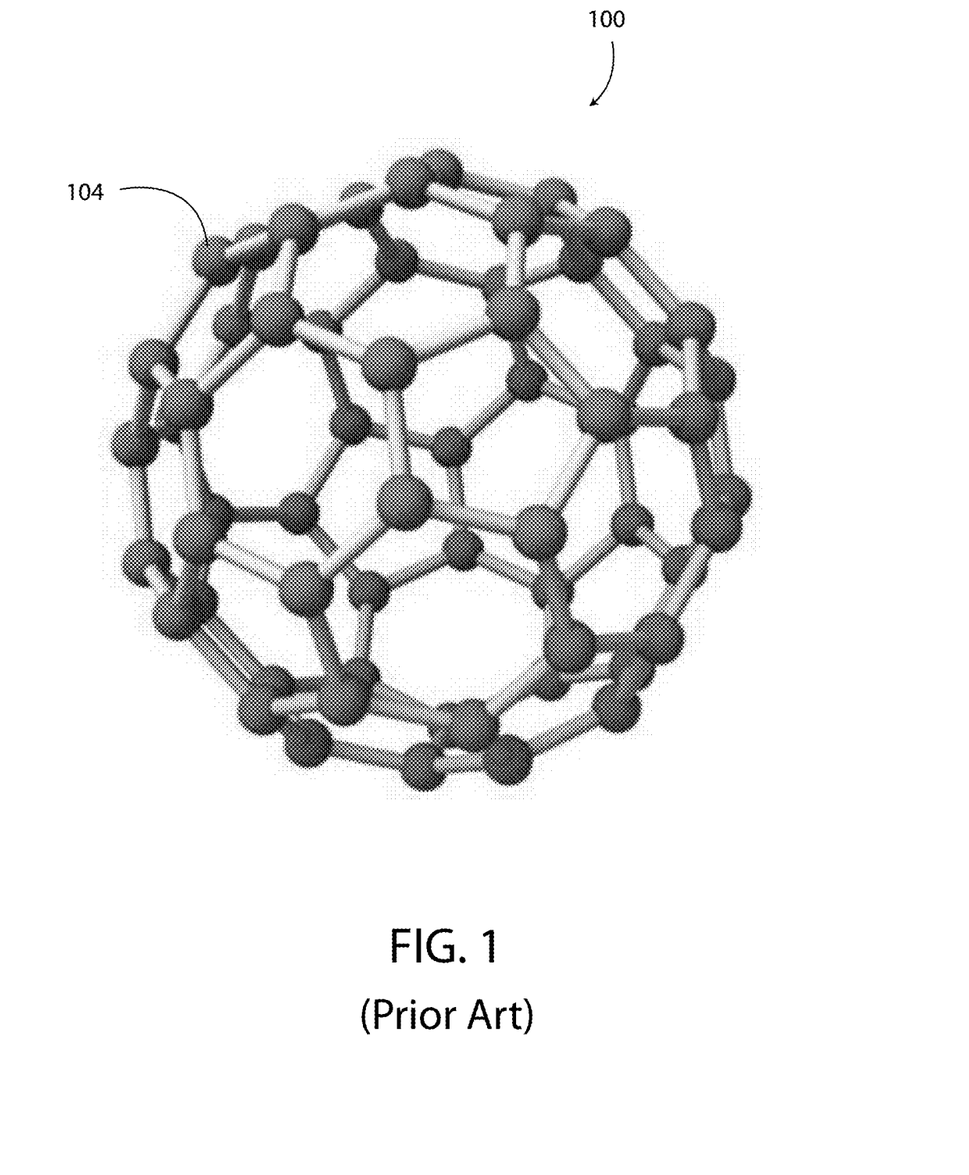
FIG. 1 is a block diagram of a C60 molecule.

As shown in FIG. 1, a C60 molecule 100 includes sixty atoms of carbon 104 arranged in a soccer ball-like shape. As used herein, the term "C60" refers to a plurality of the C60 molecules 100. C60 is available as a powder that is formed by pulverizing masses or crystals of C60. When ingested, C60 is a powerful antioxidant and free radical scavenger. C60 also provides numerous other health and nutritional benefits to humans and animals, such as reducing inflammation, increasing energy, reducing symptoms of arthritis, increasing longevity, and protecting against excessive and uncontrolled free radical exposure as occurs in many disease states. Additional health benefits of C60 are described herein.

An obstacle to administering C60 is that the C60 molecules 100 tend to clump together in masses, especially when prepared according to known processes including edible oil mixtures, such as olive oil mixtures. As such, it is difficult to administer or to dose a predetermined amount of C60, because of the heterogeneous, non-homogenous, and/or non-uniform distribution of the C60 molecules 100 in the oil. Moreover, known solvents in which C60 is readily dissolvable are not food-grade, are inedible, are toxic, and/or are not safe for human consumption. For example, C60 dissolves in solvents such as carbon disulfide, 1-chloronapthalene, toluene, and p-xylene (xylene), all of which are toxic and inedible. Table 1, included herein, identifies the solubility of C60 in various solvents. C60 dissolves only to a trivial extent in olive oil (0.9 mg/ml), and the process of breaking up clumps of the C60 molecules 100 in the olive oil is laborious, inconsistent, and largely ineffective.

In an unexpected breakthrough, C60 is dissolved in a limonene composition to form a mixture including dissolved C60 that is homogenous and stable. As used herein, the limonene composition includes limonene and/or d-limonene. The limonene composition may include 100% limonene, 100% d-limonene, and mixtures of limonene and d-limonene.

Limonene and d-limonene are excellent liquid media for dissolving C60 molecules 100. Limonene is a colorless and transparent liquid aliphatic hydrocarbon classified as a cyclic terpene, and is a major component in the oil of citrus fruit peels. Limonene is a chiral molecule. Limonene has a very low toxicity, and humans are rarely allergic to limonene. Limonene assists in the absorption of other terpenoids and chemicals through the skin, mucous membranes, and digestive tract. Limonene has immunostimulant properties. Limonene is also used as a botanical insecticide.

D-limonene is the d-isomer of limonene and has a strong smell of oranges and a bitter taste. D-limonene is used as a fragrance ingredient in cosmetic products and also as a flavoring agent in food manufacturing. D-limonene and limonene are food-grade, edible, non-toxic, and safe for human and animal consumption and ingestion. D-limonene, which is a monoterpene, is obtained commercially from citrus fruits through centrifugal separation or steam distillation, for example. D-limonene is a colorless and transparent liquid. D-limonene is plentiful and inexpensive.

Figure 2:
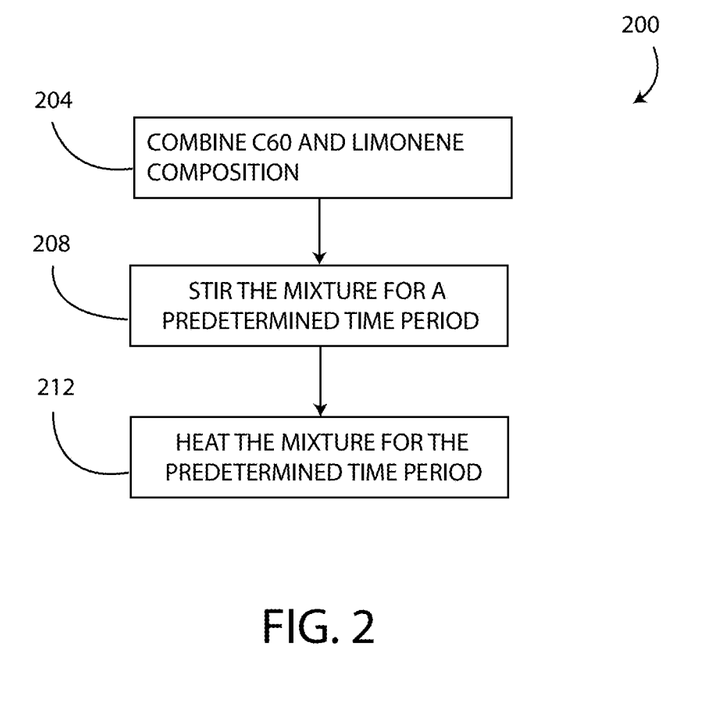
FIG. 2 is a flowchart illustrating an exemplary method of dissolving C60 molecules in a limonene composition to form an edible, food-grade, dissolved C60 mixture.
Figure 3:
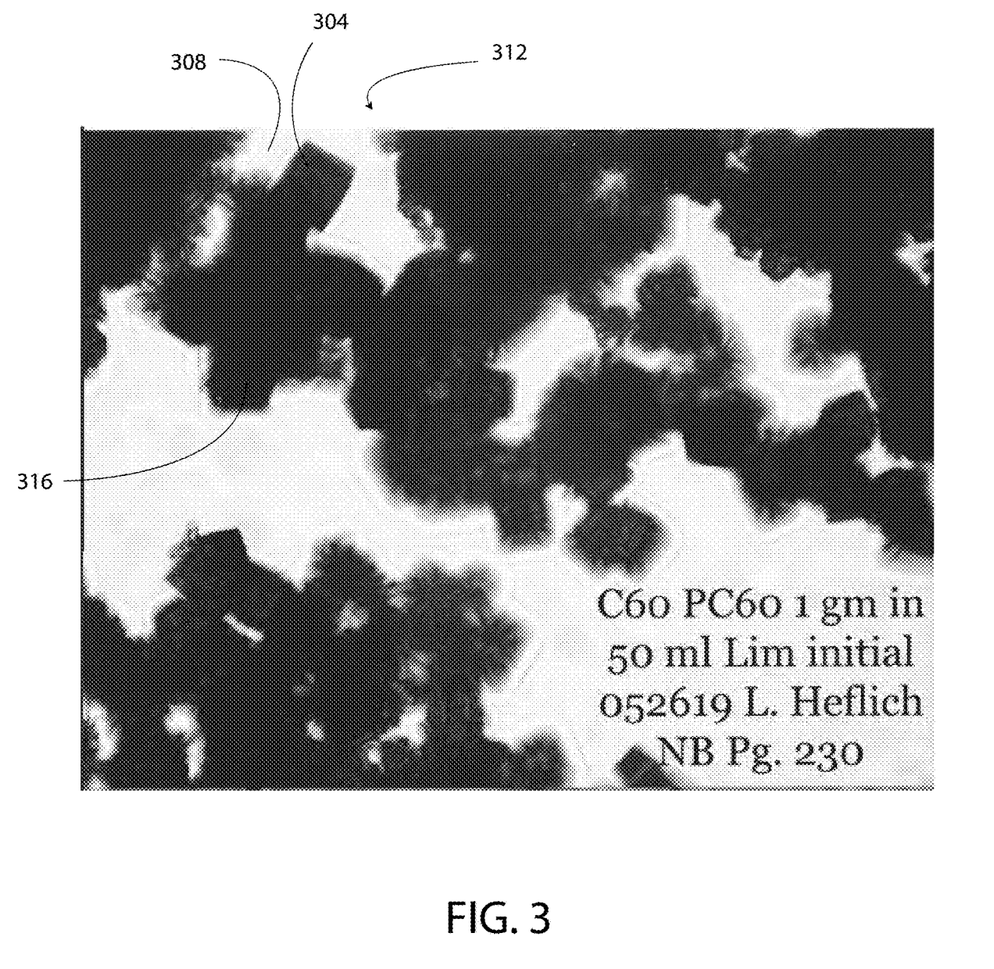
FIG. 3 is a plan view at 1000× magnification showing C60 combined with the limonene composition at the beginning of the method of FIG. 2.

As shown in the flowchart of FIG. 2 and with additional reference to FIG. 3, a method 200 for dissolving C60 304 in a liquid medium that is non-toxic and safe for human consumption includes combining C60 304 with a limonene composition 308 to form a C60 mixture 312. (Block 204). The limonene composition 308 is discussed in connection with the method 200, but the limonene composition 308 may be substituted with orange terpenes or other edible and non-toxic terpenes (or terpene containing liquids). The limonene composition 308 is used over orange terpenes, because the limonene composition 308 has a more pleasant and less bitter taste. In one embodiment, the limonene composition 308 is at least 95% d-limonene by volume, with the remaining 5% including any other liquid, such as limonene, flavoring, fragrances, and the like. In another embodiment, the limonene composition 308 is at least 75% d-limonene with the remaining 25% including any other liquid, such as limonene, flavoring, fragrances, and the like.

At block 204 of the method 200, the C60 304 is pulverized into a powdered form and combined with the liquid limonene composition 308 in a glass vessel (not shown) or any other heat-safe and non-reactive container. Additionally or alternatively, the C60 304 is not pulverized and is added to the limonene composition 308 in a granular, chunky, or crystalline state.

In FIG. 3, the C60 mixture 312, which includes the C60 304 and the limonene composition 308, is illustrated at room temperature of about 70° F. (21° C.). Specifically, FIG. 3 is a 1000× magnification view of one gram (1 g) of pulverized C60 304 mixed with sixty milliliters (60 ml) of the limonene composition 308. The molecules of the C60 304 have formed small clumps 316 and have not immediately dissolved into the limonene composition 308. Moreover, when viewed in color, the limonene composition 308 is colorless and transparent, and the C60 304 has a mostly black color. Any apparent color of the limonene composition 308 in FIG. 3 is the result of an incandescent light source giving the limonene composition 308 a yellowish hue in certain photographic representations.

Next, at blocks 208 and 212 of the method 200, the C60 mixture 312 is stirred and heated for a predetermined time period. An exemplary predetermined time period is from twenty to forty minutes. In one embodiment, the predetermined time period is thirty minutes or approximately thirty minutes.

The C60 mixture 312 is stirred with a magnetic stirring system (not shown) that uses a rotating magnetic field to cause a stir bar immersed in the C60 mixture 312 to move. In other embodiments, any other stirring system may be utilized to stir the C60 mixture 312 including hand stirring with a suitable tool, such a glass stirrer shaft (not shown). Moreover, in other embodiments, no stirring of the C60 mixture 312 is performed and only the heating process is used to dissolve the C60 304 into the limonene composition 308.

The C60 mixture 312 is heated during the predetermined time period to a predetermined temperature by a hot plate or any other electric heating element system. An exemplary predetermined temperature is from approximately 250° F. to approximately 300° F. (121° C. to 149° C.). In one embodiment, the predetermined temperature is 275° F. (135° C.) or approximately 275° F. (135° C.). Additionally or alternatively, the C60 mixture 312 is covered during the heating process (block 212), such as with a watch glass or any other suitable cover, to facilitate solvent reflux, returning the condensed solvent (i.e. the limonene composition 308) to the body of the solution.

Figure 4:
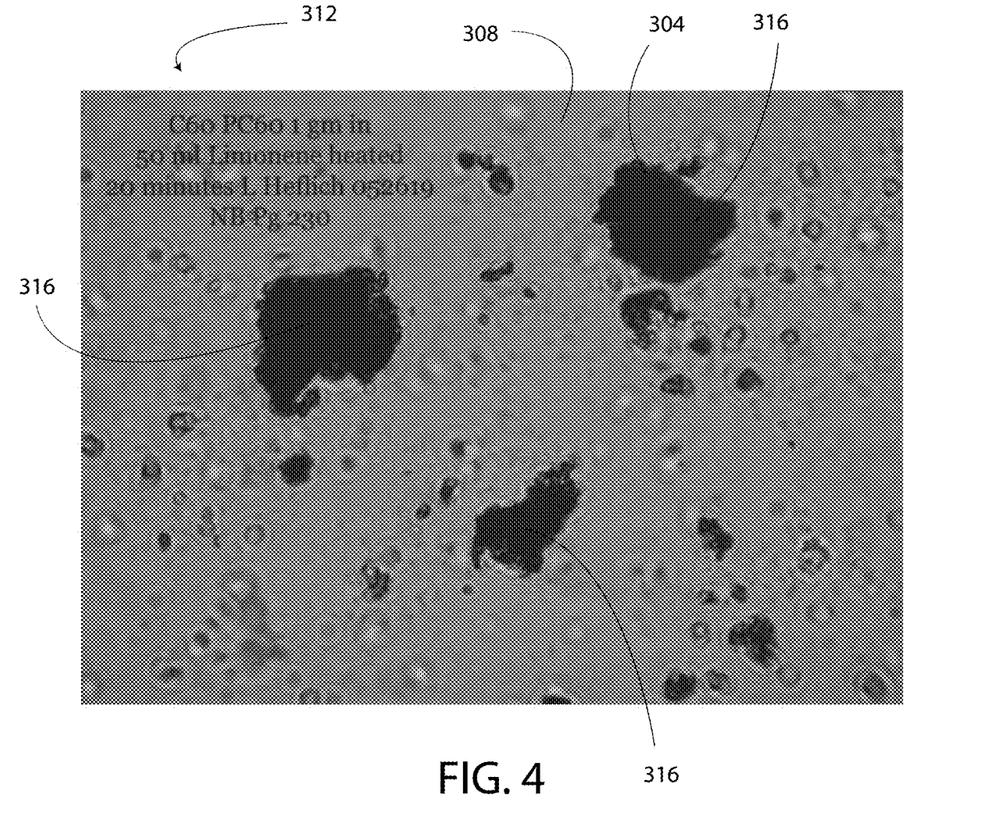
FIG. 4 is another plan view at 1000× magnification showing the C60 and limonene composition twenty minutes into the method of FIG. 2.
Figure 5:
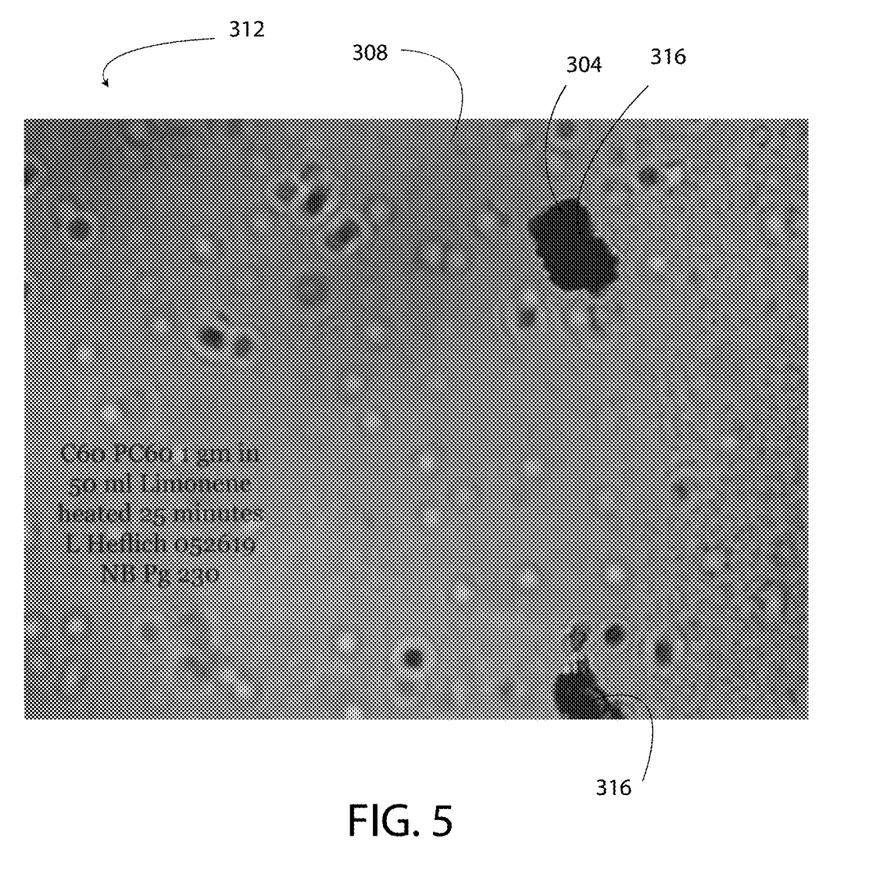
FIG. 5 is a further plan view at 1000× magnification showing the C60 and the limonene composition twenty-five minutes into the method of FIG. 2.

The stirring and heating of blocks 208 and 212 dissolves the C60 304 into the limonene composition 308. FIGS. 4 and 5 illustrate two additional stages of the stirring and heating process. In FIG. 4, the mixture 312 has been heated for twenty minutes and fewer clumps 316 of the C60 304 remain, as compared to FIG. 3, thereby indicating that more molecules of the C60 304 have dissolved into the limonene composition 308. When viewed in color, the C60 mixture 312 has become orange at the process stage illustrated in FIG. 4.

In FIG. 5, the C60 mixture 312 has been heated for twenty-five minutes and even fewer of the clumps 316 of the C60 304 remain, as compared to FIG. 4. The remaining clumps 316 of the C60 304 are very small. When viewed in color, the C60 mixture 312 has an orange color at the process stage illustrated in FIG. 5.

Figure 6:
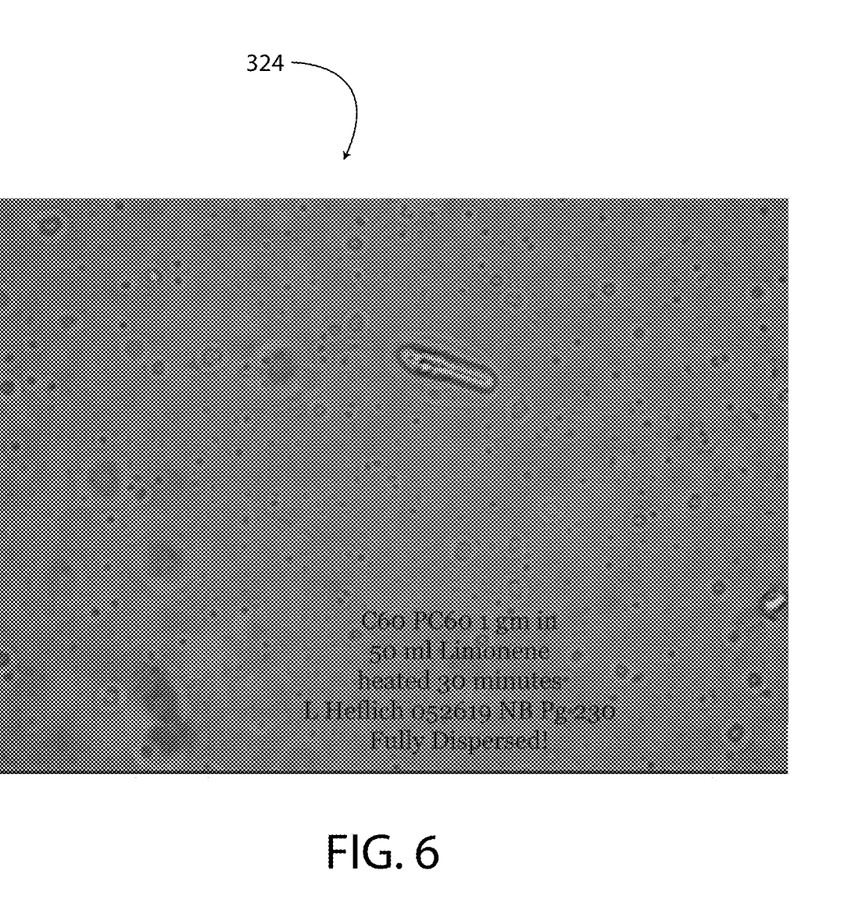
FIG. 6 is yet another plan view at 1000× magnification showing the C60 and the limonene composition thirty minutes into the method of FIG. 2 and illustrating the dissolved C60 mixture.

In FIG. 6, the C60 mixture 312 has been heated for thirty minutes and no clumps 316 of the C60 304 remain, indicating that in FIG. 6, a dissolved C60 mixture 324 is formed. As used herein, the dissolved C60 mixture 324 is a homogenous liquid including molecules of the C60 304 that are fully dissolved into the limonene composition 308 with no clumps 316 of the C60 304. The dissolved C60 mixture 324 is a clear solution (i.e. transparent) with a deep magenta color. Any artifacts illustrated in FIG. 6 are air bubbles or other features, but are not clumps 316 of the C60 304.

In some embodiments, at blocks 208 and 212 of the method 200, the C60 mixture 312 is sonicated to increase further the dissolution of the C60 304 into the limonene composition 308 and to assist in breaking up any of the clumps 316 of the C60 304. Sonication is a process of applying sound energy to the C60 mixture 312, thereby agitating the clumps 316 of the C60 304 and promoting full and timely dissolution of the molecules of the C60 304 into the limonene composition 308. A sonication system (not shown) may be placed near or in the C60 mixture 312 to perform the sonication.

As used herein, "dissolving" the C60 304 into the limonene composition 308 refers to forming a solution including a homogenous mixture of C60 molecules 100 (FIG. 1) and molecules of the limonene composition 308. In such a solution, the C60 304 is the solute and the limonene composition 308 is the solvent. In some embodiments, atomic level changes and bonds may occur between the dissolved C60 molecules 100 and molecules of the limonene composition 308; however, the C60 molecules 100 retain their shape as shown in FIG. 1 and also retain their therapeutic, nutritional, medicinal, and health benefits. The dissolved C60 mixture 324 may also be referred to as a C60 solution 324 including solubilized C60 304 in the limonene composition 308.

In an exemplary embodiment of the dissolved C60 mixture 324 made according to the method 200 of FIG. 2, the dissolved C60 mixture 324 includes 16.67 mg of dissolved C60 304 per one milliliter (1 ml) of the limonene composition 308. At the solubility of 16.67 mg/ml, the dissolved C60 mixture 324 is "stable," meaning that no settling or precipitating of the C60 304 occurs in the limonene composition 308, even after six weeks of sitting at room temperature. As disclosed herein, a limit of solubility of the C60 304 in the limonene composition 308 is from approximately 16.67 mg/ml to approximately 20.0 mg/ml. Accordingly, in other embodiments, the dissolved C60 mixture 324 includes from 0.50 mg to 20.0 mg of the dissolved C60 304 per one milliliter (1 ml) of the limonene composition 308.

When the dissolved C60 mixture 324 is made according to the method 200 of FIG. 2 with more than 16.67 mg of C60 304 per milliliter of the limonene composition 308, some settling of the C60 304 occurs when the dissolved C60 mixture 324 is cooled from the predetermined temperature to room temperature. The settled C60 304, however, can be easily "redissolved" by gently shaking and/or agitating the dissolved C60 mixture 324 at room temperature (i.e. without reheating). Whereas, when the dissolved C60 mixture 324 is made according to the method 200 of FIG. 2 with 16.67 mg or less of the C60 304 per milliliter of the limonene composition 308, no settling of the C60 304 occurs when the dissolved C60 mixture 324 is cooled from the predetermined temperature to room temperature, and the dissolved C60 mixture 324 is stable. For a point of reference, the limit of solubility of the C60 304 in toluene is 2.8 mg/ml and the limit of solubility of the C60 304 in olive oil is 0.9 mg/ml. Thus, the method 200 produces an edible solution with a high quantity of dissolved C60 molecules 100 per milliliter of solvent.

The method 200 of FIG. 2 works to dissolve all of the commercially available forms of C60 304 including those types of C60 304 having a snowflake appearance under magnification and those types of C60 304 having a crystalline (i.e. cubic or hexagonal) appearance under magnification.

As noted above, the stirring process of block 208 is optional, but the heating process of block 212 is typically performed. As disclosed herein, the C60 304 typically does not dissolve to any significant extent into the limonene composition 308 when the C60 mixture 312 is at room temperature 70° F. (21° C.). According to the unexpected breakthrough discovered herein, however, when the limonene composition 308 and the C60 mixture 312 is heated dissolution of the C60 304 occurs. As such, the method 200 is different than the process of mixing C60 304 in olive oil, which occurs at room temperature 70° F. (21° C.) over the course of many days without heating. In such a process, heating the olive oil does not produce any significant increase of solubility of C60 304, and does not produce any significant decrease in the mixing time. Moreover, heating the olive oil in an attempt to increase solubility of C60 304 fouls the olive oil, making the olive oil have an undesirable burnt taste and appearance. As such, the known olive oil process of mixing the C60 304 cannot be made more efficient by heating the olive oil. The known properties of C60 304 when mixed with olive oil make the high solubility of C60 304 in the heated limonene composition 308 even more of a surprise and a breakthrough.

The method 200 is orders of magnitude faster than the process of mixing C60 304 in olive oil. Mixing C60 304 in olive oil takes approximately seven days in order to break up the clumps of C60 304, and over the course of the seven days, only a trivial amount of the C60 304 is actually dissolved in the olive oil with the rest of the C60 304 being unevenly dispersed through the olive oil in small (e.g. microscopic) clumps. The method 200, as disclosed herein, dissolves the C60 304 in only thirty minutes, thereby offering huge time savings in preparing an edible, non-toxic, liquid-based dissolved C60 mixture 324.

The dissolved C60 mixture 324 of the present disclosure provides a convenient means of dosing a predetermined amount of the C60 304 by easily measuring a liquid quantity of the dissolved C60 mixture 324. That is, a known amount of the C60 304 can be dosed when the amount of the C60 304 and the amount of the limonene composition 308 used to form the dissolved C60 mixture 324 are known. For example, in an embodiment having one gram (1 gm) of the C60 304 and sixty milliliters (60 ml) of the limonene composition 308, each milliliter of the dissolved C60 mixture 324 contains 16.67 mg of the C60 304, since very little of the limonene composition 308 evaporates during the method 200.

The dissolved C60 mixture 324 is edible, safe, and non-toxic and is suitable for therapeutic and nutritional dosing of the C60 304 and the corresponding C60 molecules 100. Additionally, the dissolved C60 mixture 324 has a pleasant citrus taste and aroma. The dissolved C60 mixture 324 can be administered orally and swallowed, or administered orally and retained in the mouth for sublingual or buccal administration. The dissolved C60 mixture 324 can also be included in a topical cream for application to the skin and for transdermal administration of the C60 molecules 100. The dissolved C60 mixture 324 can be included in a liposomal dispersion for convenient oral administration.

The dissolved C60 mixture 324 is also highly bioactive. As used herein, "bioactive" means functional as an antioxidant. Clumped or undissolved C60, as is found in known olive oil mixtures, has little to no bioactivity and does not effectively migrate through cell walls and mitochondrial walls. Moreover, clumped or undissolved C60 is filtered out of the blood by the liver or the intestinal wall, thereby further preventing and/or limiting the bioactivity of the C60 molecules 100. The dissolved C60 mixture 324 is about 18.5× (i.e. (16.67 mg/ml)/(0.9 mg/ml)) more bioactive than olive oil mixtures including C60 (by volume), because the dissolved C60 mixture 324 includes orders of magnitude more dissolved C60 molecules 100 than is possible with any C60 and olive oil mixture.

The bioactive effect of the dissolved C60 mixture 324, in one embodiment, occurs when the C60 molecules 100 migrate through cell walls and mitochondrial walls and come into contact with free radicals. Specifically, the C60 molecules 100 pass through cell walls and the blood/brain barrier to enter mitochondria, where most of the short-lived, highly reactive and, therefore, dangerous free radicals are produced. Consider in an example, the very damaging hydroxyl free radical, which exists on average for less than one ten billionth of a second, but during this time can negatively react with organic material inside a cell mitochondria. The highly-bioactive dissolved C60 mixture 324 enables the C60 molecules 100 to migrate into the mitochondria where the hydroxyl free radical and other free radicals are produced. The C60 molecules 100 neutralize the hydroxyl free radical and other free radicals by absorbing and/or sequestering free electrons from the free radicals. The free electrons are held inside of the carbon "cage structure" (see FIG. 1) of the C60 molecule 100, and cannot escape. Other antioxidants absorb and/or sequester one free electron by holding the free electron on the surface of the antioxidant where the free electron can react and create additional free radicals. Whereas, C60 molecules 100 of the dissolved C60 mixture 324 absorb and/or sequester up to thirty-four electrons each and remain stable. The C60 molecules 100 of the dissolved C60 mixture 324 diffuse throughout the entire body and then diffuse out of the body with a residence time of about five days, taking with them the sequestered and stabilized free electrons.

Figure 7:
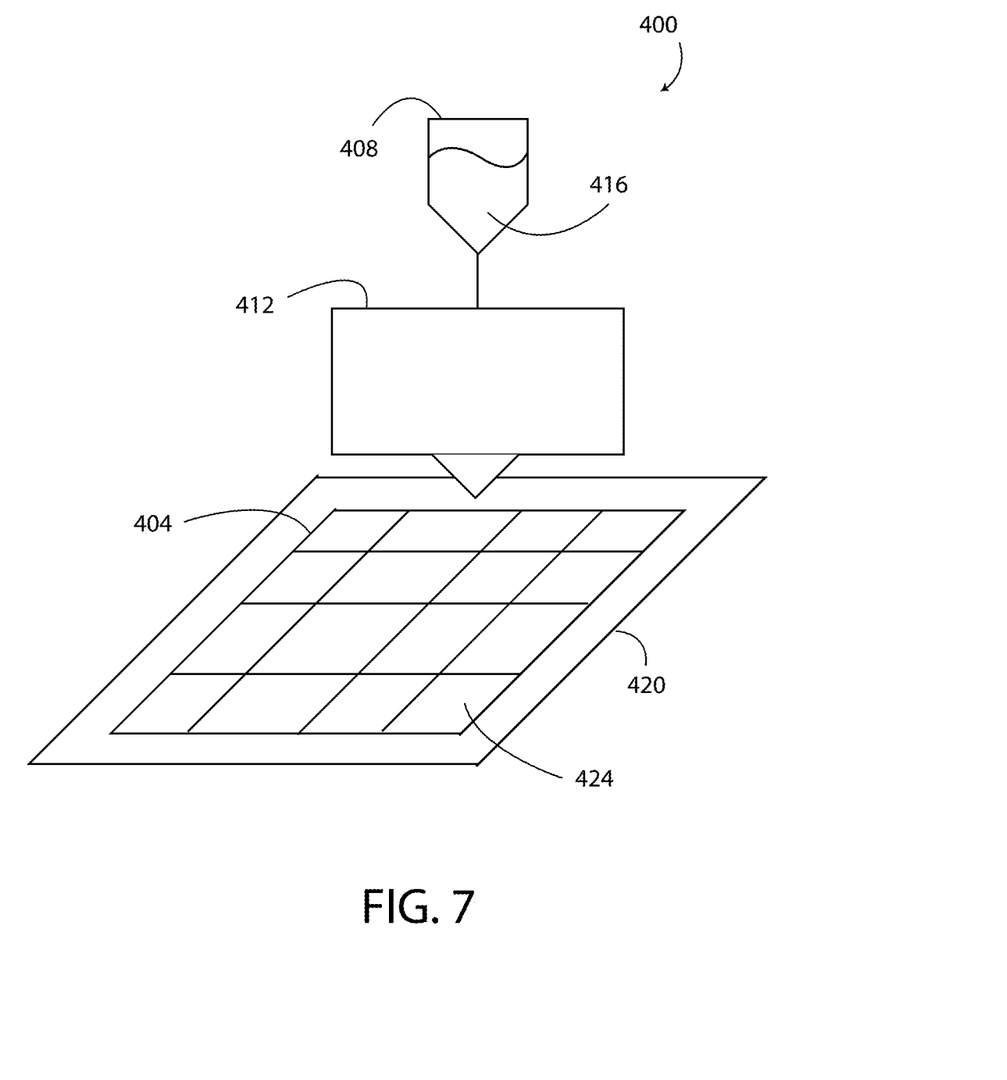
FIG. 7 is a block diagram illustrating a system for forming an orally dissolvable thin film including C60 molecules using the dissolved C60 mixture of FIG. 6.

As shown in FIG. 7, a system 400 is configured to prepare an orally dissolving edible thin film 404 including the C60 molecules 100. The thin film 404 including the C60 molecules 100 is also referred to herein as a therapeutic dosage form. A dosage form is a structure such as a pill, a capsule, a tablet, and in this example, a thin film. The dosage form delivers a particular dose of a substance, which in this disclosure is a particular dose of the C60 molecules 100.

The system 400 includes a container 408 fluidically connected to a thin film forming unit 412. The container 408 contains a combination of the dissolved C60 mixture 324 (made according to the method 200) and a thin film liquid to form a thin film mixture 416. The thin film forming unit 412 sprays or deposits the thin film mixture 416 onto a base 420 or a polished steel belt to form the thin film 404. The thickness of the thin film 404 is about 0.1 mm. The thin film 404 is then cut into pieces 424 (i.e. the therapeutic dosage form) having a predetermined area based on a desired dosage of the C60 molecules 100, for example. An exemplary predetermined area is approximately six square centimeters (6 cm$^2$).

Since the C60 molecules 100 are evenly and fully dissolved in the dissolved C60 mixture 324 only a brief (a few seconds to one minute) mixing time is required to evenly and fully distribute the C60 molecules 100 of the dissolved C60 mixture 324 throughout the thin film liquid when forming the thin film mixture 416. Moreover, due to the full dissolution of the C60 molecules 100 in the dissolved C60 mixture 324, the orally dissolvable thin film 404 has a predetermined amount of bioactive C60 molecules 100 per unit of area of the thin film 404. For example, in one embodiment, the thin film 404 includes twenty micrograms (20 µg) of the C60 molecules 100 per square centimeter of the thin film 404. The C60 molecules 100 are homogeneously dispersed throughout the thin film 404.

In an exemplary embodiment, the thin film liquid of the thin film mixture 416 is formed from or includes pullulan, which is a polysaccharide polymer that is edible, mostly tasteless, and is easily and quickly dissolvable in the mouth. The thin film liquid may also include gum arabic or any other chemical typically used in the production of orally dissolvable thin films.

The therapeutic dosage form 424 includes an effective dose of the C60 molecules 100. An effective dose is an amount of the C60 molecules 100 that is sufficient or desirable for providing a therapeutic, nutritional, and/or medicinal effect. An exemplary effective dose is approximately twenty micrograms (20 µg) of the C60 molecules 100. Since the thin film 404 includes a homogenous mixture of the C60 molecules, the effective dose is easily determined based on the area of the therapeutic dosage form 424. The therapeutic dosage form 424 is stable and has a long shelf life, unlike the olive oil and C60 mixture.

Figure 8:
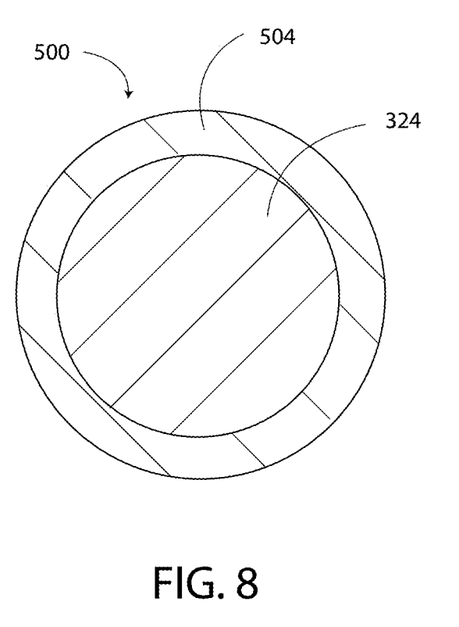
FIG. 8 is a cross sectional view of a liposome including the dissolved C60 mixture of FIG. 6.

In some embodiments, the thin film mixture 416 is an emulsion that is sprayed or deposited on the base 420. In another embodiment, as illustrated in FIG. 8, instead of mixing directly the dissolved C60 mixture 324 with the thin film liquid, the dissolved C60 mixture 324 is first mixed with a phospholipid 504 to form a plurality of liposomes 500. Each of the liposomes 500 includes a shell of the phospholipid 504 surrounding or encapsulating a quantity of the dissolved C60 mixture 324. The liposomes 500 are mixed with the thin film liquid to form the thin film mixture 416 that is sprayed or deposited on the base 420. The resulting thin film 404 includes liposomes 500 uniformly and homogeneously dispersed throughout the orally dissolvable thin film 404.

In another embodiment, the dissolved C60 mixture 324 is combined with a medication that is suitable for topical, intravenous, oral, intra-articular, or transcutaneous administration methods. For example, in one embodiment, the dissolved C60 mixture 324 is combined with cortisone and/or dapsone and is administered to a patient according to at least one of the administration methods listed above.

Figure 9:
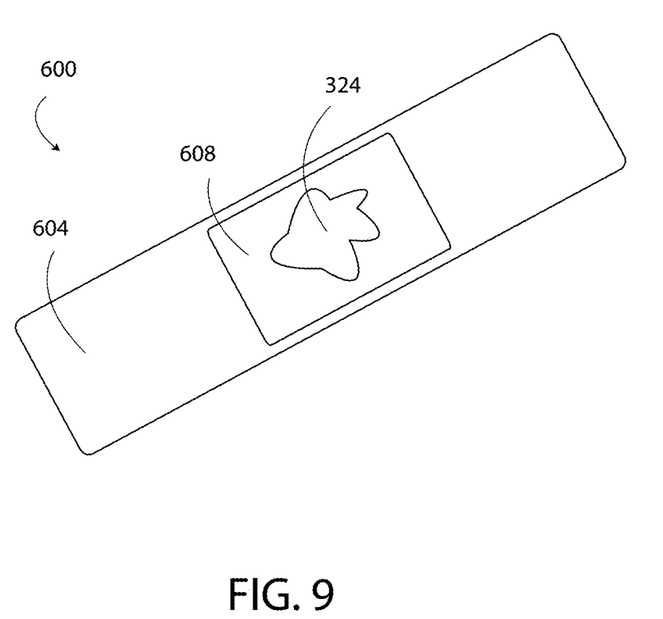
FIG. 9 is a block diagram illustrating an adhesive bandage including the dissolved C60 mixture of FIG. 6.

As shown in FIG. 9, an adhesive bandage 600 (i.e. a Band-Aid® brand bandage) includes the dissolved C60 mixture 324. The bandage 600 includes an adhesive strip 604, a pad 608 mounted on the adhesive strip 604, and the dissolved C60 mixture 324 applied to the pad 608. The adhesive strip 604 is configured to adhere to the skin of a user with the pad 608 placed over a wound and/or in contact with the wound. When the bandage 600 is adhered to a user, the dissolved C60 mixture 324 is topically applied to the wound from the pad 608. The dissolved C60 mixture 324 aids in healing of the wound by at least reducing inflammation at the wound site and reducing free radicals at the wound site that prevent healing.

The method 200 of producing the dissolved C60 mixture 324 is distinguished from a mixture of C60 and olive oil based on the amount of the C60 304 that is dissolved in the solvent. For example, in the mixture of C60 and olive oil, only a trivial amount of the C60 actually dissolves in the olive oil even after one week of stirring. In the method 200, however, up to approximately 16.67 mg of the C60 304 per one milliliter (1 ml) of the limonene composition 308 is fully dissolved in the dissolved C60 mixture 324. As such, the dissolved C60 mixture 324 includes more bioactive C60 molecules 100 by volume than any mixture of C60 and olive oil, and is also easier and faster to produce. The dissolved C60 mixture 324 and the associated method 200 is and/or produces a soluble form of C60 304 using an edible food grade solvent (i.e. the limonene composition 308), which enables the human body to benefit from the full therapeutic, medicinal, and health effects of the C60 304, as compared to existing C60 mixtures using olive oil and the like.

The C60 mixture 324 is well-suited for administering to patients (both human and animal) during tests of the therapeutic, medical, and health benefits of C60 304 unlike mixtures of C60 and olive oil. Tests done to date using C60 and olive oil, are largely invalid because C60 dissolves only to a trivial extent in olive oil and the resultant mixture includes mostly undissolved and non-bioactive clumps of C60. Therefore, doses of the C60 and olive oil mixture have an inaccurate, unknowable, and/or inconsistent amount of C60 included therein. The tests are largely invalid, because the subjects were not given a precise amount of C60 with some subjects likely to have received little to no bioactive C60 in their dosage. The clumped and undissolved C60 in an olive oil mixture is removed by filtering mechanisms in the body, including the intestines, liver, and lungs and potentially even results in disease. Discovering a safe and stable way to dissolve the C60 304 (as is done by the method 200) enables accurate dosing, facilitates free movement of the C60 molecules 100 throughout the body in minutes, and permits the C60 molecules 100 to pass through cell membranes in order to be located inside cells and inside mitochondria where most free radicals are produced. The result is a reduction in damage to proteins, fats, and DNA caused by highly-reactive, short-lived, free radical molecules produced as a natural byproduct of respiration and intense exercise. For example, cell respiration and energy production by the breakdown of glucose yields three free radicals per glucose molecule of hydrogen peroxide and hydroxyl radicals. C60 molecules 100 bond to these free radicals and remove them from the body. In addition, the C60 mixture 324 protects against environmental free radicals from exposure to UVA and UVB from intense sunlight, air pollution, cigarette smoke, and cosmic rays from high altitude airplane travel. Moreover, uncontrolled free radical production by the body is the causative factor of cellular damage and disease symptoms in almost all diseases. These diseases start out with a normal response of the body to foreign material, which is the production of free radicals to destroy the foreign material. For unknown reasons, the control mechanism gets stuck in the "on" position, resulting in the continued production of free radicals. The free radicals cause cellular damage, which then results in inflammation, and further production of free radicals in an increasing and uncontrolled spiral that results in the symptoms of the disease. There is evidence that C60 may be able to stop the overproduction of free radicals, allowing the body to repair, stopping the disease spiral.

With reference again to FIG. 1, the antioxidant properties of the C60 molecules 100 are based on the thirty-two aromatic rings of alternating conjugated double bonds with lowest unoccupied molecular orbitals (LUMO), which enable the molecule 100 to easily take up an electron from reactive oxygen species (e.g. free radicals). Free electrons from up to thirty-four methyl radicals have been absorbed onto a single C60 molecule 100. The quenching process is catalytic, such that the C60 molecule 100 can react with many superoxide molecules without being consumed. Due to this feature, C60 molecules 100 are the most efficient radical scavenger and are described as radical "sponges." An advantage of using C60 molecules 100 as an antioxidant is their ability to localize within the cell, such as in mitochondria and other cell compartment sites, where, in healthy and especially in diseased states, the production of destructive free radicals takes place.

Excess free radicals have been implicated in cell damage or death, neurologic damage, diseases such as Alzheimer's, Lou Gehrig's disease (ALS), cardiovascular disease, diabetes, hypertension, irritable bowel syndrome (IBS), autism, atherosclerosis among many others. Additional areas of potential application of the dissolved C60 mixture 324 include: radioprotective effects, burn dressing, chronic wound healing, osteoporosis, preventing UVA and UVB damage to skin, treating viral infections, and psoriasis.

The dissolved C60 mixture 324 and the method 200 opens the door to medical applications of C60, including: antiviral, antioxidant, anti-inflammatory, enabling photo induced biological activities, as a potential scaffold for photodynamic therapy and diagnostic applications, as a carrier for gene and drug delivery systems, and in serum protein profiling as material-enhanced laser desorption/ionization (MELDI) material for biomarker discovery.

As set forth above, the concentration of solubilized C60 achieved in the dissolved C60 mixture 324 and by the method 200 is much higher than achieved by other edible solvents. This higher concentration enables further innovation in terms of the delivery format of the C60 molecules 100. Known edible C60 mixtures are extremely low solubility liquid-based delivery formats, i.e. olive oil. The method 200 and the dissolved C60 mixture 324 enables the development of a product in edible strip format due to the higher concentration of soluble C60 molecules 100. Moreover, as shown in Table 1, d-limonene is the only known safe and edible solvent that has sufficient solubility to be practical for preparation and use in developing products that deliver non-trivial amounts of solubilized and bioactive C60. In Table 1, "ND" indicates that C60 in insoluble in the identified solvent. The solubility of C60 in d-limonene is included in the chart according to the results achieved by the method 200 and was not previously known in the art.

TABLE 1

Solubility of C60 in Various Solvents

| Solvent | Solubility Limit in mg/ml | Edible |
| --- | --- | --- |
| methanol | ND | No |
| tetrahydrofuran | ND | No |
| isopropanol | ND | No |
| water | $1.3 \times 10^{-11}$ | Yes |
| acetone | 0.001 | No |
| ethanol | 0.0014 | Yes |
| n-pentane | 0.005 | No |
| cyclohexane | 0.036 | No |
| octanol | 0.0429 | No |
| n-hexane | 0.043 | No |
| n-decane | 0.071 | No |
| chloroform | 0.16 | No |
| dichloromethane | 0.26 | No |
| tetrachloromethane | 0.32 | No |
| benzonitrile | 0.41 | No |
| carbon tetrachloride | 0.447 | No |
| olive oil | 0.9 | Yes |
| benzene | 1.7 | No |
| toluene | 2.8 | No |
| decalins | 4.6 | No |
| xylene | 5.2 | No |
| anisole | 5.6 | No |
| carbon disulfide | 7.9 | No |
| tetralin | 16 | No |
| d-limonene | 16.67 | Yes |
| 1,2-dichlorobenzene | 27 | No |
| 1-methylnaphthalene | 33 | No |
| 1-chloronaphthalene | 41 | No |

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of preparing an orally dissolving thin film including dissolved C60 molecules, comprising:
    combining C60 molecules with a limonene composition to form a C60 mixture;
    heating the C60 mixture to a predetermined temperature for a predetermined time period to dissolve the C60 molecules into the limonene composition to form a dissolved C60 mixture;
    combining the dissolved C60 mixture with a thin film liquid to form a thin film mixture; and
    forming an orally dissolvable thin film from the thin film mixture,
    wherein the dissolved C60 mixture is homogenous and includes at least 16.67 mg of the dissolved C60 molecules per milliliter of the limonene composition.

2. The method as claimed in claim 1, wherein the dissolved C60 mixture is stable, such that no settling or precipitating of the C60 molecules occurs.

3. The method as claimed in claim 2, wherein the limonene composition is at least 95% d-limonene by volume.

4. The method as claimed in claim 1, further comprising:
    mixing the dissolved C60 mixture with a lipid to form a plurality of liposomes; and
    combining the plurality of liposomes with the thin film liquid,
    wherein the liposomes of the plurality of liposomes are uniformly dispersed throughout the orally dissolvable thin film.

5. The method as claimed in claim 1, wherein the orally dissolvable thin film has a predetermined amount of the C60 molecules per unit of area of the thin film.

6. The method as claimed in claim 1, wherein:
    the orally dissolvable thin film is an ingestible therapeutic dosage form, and
    the C60 molecules are dispersed homogenously throughout the orally dissolvable thin film.

7. The method as claimed in claim 6, further comprising:
administering orally the orally dissolvable film.

\* \* \* \* \*